(12) United States Patent
Buchan et al.

(10) Patent No.: US 10,268,784 B2
(45) Date of Patent: *Apr. 23, 2019

(54) REAL-TIME PREDICTIVE SIMULATION MODELING

(71) Applicant: CERNER INNOVATION, INC., Kansas City, KS (US)

(72) Inventors: Amber Buchan, Overland Park, KS (US); Hugh Ryan, Jr., Lee's Summit, MO (US); Teresa Smith, Blue Springs, MO (US); Bharat Sutariya, Parkville, MO (US)

(73) Assignee: CERNER INNOVATION, INC., Kansas City, KS (US)

( * ) Notice: Subject to any disclaimer, the term of this patent is extended or adjusted under 35 U.S.C. 154(b) by 525 days.

This patent is subject to a terminal disclaimer.

(21) Appl. No.: 14/804,963

(22) Filed: Jul. 21, 2015

(65) Prior Publication Data
US 2015/0324504 A1  Nov. 12, 2015

Related U.S. Application Data

(63) Continuation of application No. 12/981,779, filed on Dec. 30, 2010, now Pat. No. 9,117,183.

(51) Int. Cl.
*G06G 7/48* (2006.01)
*G06F 17/50* (2006.01)
(Continued)

(52) U.S. Cl.
CPC ......... *G06F 17/5009* (2013.01); *G06Q 10/06* (2013.01); *G06Q 50/22* (2013.01); *G16H 40/20* (2018.01)

(58) Field of Classification Search
CPC .... G06F 17/5009; G06F 19/327; G06Q 50/22
See application file for complete search history.

(56) References Cited

U.S. PATENT DOCUMENTS

| 7,925,603 B1 * | 4/2011 | Laigid ................... G06Q 10/04 706/45 |
| 2010/0083164 A1 * | 4/2010 | Martin ................ G06F 19/3406 715/781 |

(Continued)

OTHER PUBLICATIONS

Vassilacopoulos, G., "A Simulation Model for Bed Allocation to Hosital Inpatient Departments", Nov. 1985, Simulation, 45:5.*

(Continued)

*Primary Examiner* — Cedric Johnson
(74) *Attorney, Agent, or Firm* — Shook, Hardy & Bacon, L.L.P.

(57) ABSTRACT

Methods, systems, and computer storage media are provided for generating simulation graphs using real-time clinical data. A user may indicate one or more scenario variables to apply to an area of interest. A simulation graph is then generated that includes at least an indication of a scenario status. The scenario status indicates an expected result based on the one or more scenario variables selected by the user. The simulation graph may also include a baseline status indicating an expected result should no changes be made to a current environment. Multiple simulation graphs for varying areas of interest may be generated and compared to one another such that a user is able to quickly identify efficient solutions.

20 Claims, 12 Drawing Sheets

(51) Int. Cl.
*G06Q 10/06* (2012.01)
*G06Q 50/22* (2018.01)
*G16H 40/20* (2018.01)

(56) References Cited

U.S. PATENT DOCUMENTS

2010/0324926 A1* 12/2010 Rosow ............... G06Q 10/02
 705/2
2011/0125539 A1 5/2011 Bollapragada et al.

OTHER PUBLICATIONS

Draeger, Margaret A., "An Emergency Department Simulation Model Used to Evaluate Alternative Nurse Staffing and Patient Population Scenarios", 1992, Proceedings of the 1992 Winter Simulation Conference.*

Marmor, Yariv N. et al., "Toward Simulation-Based Real-Time Decision-Support Systems for Emergency Departments", 2009, Proceedings for the 2009 Winter Simulation Conference, IEEE.*

Altinel, I. Kuban et al., "Simulation Modeling for Emergency Bed Requirement Planning", 1996, Annals of Operations Research 67, J.C. Baltzer AG.

Marmor, Yariv, Emergency-Departments Simulation in Support of Service-Engineering: Staffing, Design, and Real-Time Tracking, Feb. 2010, Israel Institute of Technology, pp. 52, 53.

Vassilacopoulos, G., "A Simulation Model for Bed Allocation to Hospital Inpatient Departments", Nov. 1985, Simulation, 45: 5.

Hoot, Nathan R. et al., "Forecasting Emergency Department Crowding: A Discrete Event Simulation", Aug. 2008, Annals of Emergency Medicine, vol. 52, No. 2, American College of Emergency Physicians.

First Action Interview Preinterview Communication dated Jun. 12, 2013 in U.S. Appl. No. 12/981,779, 6 pages.

First Action Interview Office Action dated Jul. 30, 2013 in U.S. Appl. No. 12/981,779, 7 pages.

Final Office Action dated Nov. 4, 2013 in U.S. Appl. No. 12/981,779, 32 pages.

Non-Final Office Action dated May 14, 2014 in U.S. Appl. No. 12/981,779, 36 pages.

Final Office Action dated Jan. 2, 2015 in U.S. Appl. No. 12/981,779, 43 pages.

Notice of Allowance dated Apr. 21, 2015 in U.S. Appl. No. 12/981,779, 11 pages.

* cited by examiner

SIMULATION DASHBOARD

HOME > GRAPH BUILDER > SIMULATION LIBRARY

SIMULATION LIBRARY

SELECT TYPE: ALL    ENTER KEYWORD: [SEARCH]    [NEW] 510    [ADD TO GROUP] 520    [COMPARE] 530

▶ ANALYSIS GROUPS
▼ GRAPHS

| NAME | SELECT | TEMPLATE | DATE MODIFIED |
|---|---|---|---|
| AVERAGE LENGTH OF STAY PER DAY | ☐ | | 10-1-10 5:10 PM |
| TOTAL WAIT TIMES | ☐ | ☐ | 10-2-10 3:00 PM |
| UTILIZATION OVERALL | ☐ | ☐ | 10-1-10 2:06 PM |
| PATIENT LENGTH OF STAY OVERALL | ☐ | ☐ | 9-30-10 1:46 PM |
| RESOURCE LEVEL: BEDS | ☐ | | 9-30-10 10:31 AM |
| LENGTH OF STAY IF DISCHARGED | ☐ | | 9-30-10 8:04 AM |

SIMULATION DETAILS:

FIG. 5

SIMULATION DASHBOARD

HOME > GRAPH BUILDER > SIMULATION LIBRARY

SIMULATION LIBRARY

SELECT TYPE: ALL | ENTER KEYWORD: [SEARCH] /-610 [NEW] [ADD TO GROUP] [COMPARE]

▶ ANALYSIS GROUP  SET NAME: [ANALYSIS GROUP] [OK]
▼ GRAPHS

| NAME | SELECT | TEMPLATE | DATE MODIFIED |
|---|---|---|---|
| AVERAGE LENGTH OF STAY PER DAY | ☐ |  | 10-1-10 5:10 PM |
| TOTAL WAIT TIMES | ☐ | ☐ | 10-2-10 3:00 PM |
| UTILIZATION OVERALL | ☐ | ☐ | 10-1-10 2:06 PM |
| PATIENT LENGTH OF STAY OVERALL | ☐ | ☐ | 9-30-10 1:46 PM |
| RESOURCE LEVEL: BEDS | ☐ |  | 9-30-10 10:31 AM |
| LENGTH OF STAY IF DISCHARGED | ☐ |  | 9-30-10 8:04 AM |

SIMULATION DETAILS:

Sidebar: HOME, GRAPH BUILDER, SIMULATION LIBRARY

FIG. 6

REAL-TIME PREDICTIVE SIMULATION MODELING

CROSS-REFERENCE TO RELATED APPLICATIONS

This application, having U.S. Ser. No. 14/804,963 and entitled "Real-time Predictive Simulation Modeling," is a Continuation Application of co-pending U.S. application Ser. No. 12/981,779, and entitled "Real-time Predictive Simulation Modeling." This application claims the benefit of and incorporates the entirety of co-pending U.S. application Ser. No. 12/981,779, which was filed Dec. 30, 2010.

BACKGROUND

Healthcare facilities face a variety of challenges due to increasing patient demands for healthcare services. The increasing demands require healthcare facilities to provide high quality healthcare services in the most efficient way possible. To deliver the most efficient healthcare services, decisions affecting the efficiency of a healthcare environment are often required. For example, a healthcare provider may be faced with a decision to either add an extra nurse to a shift or to make another bed available in an effort to increase efficiency. The decision is difficult to make without objective evidence to assist in the decision-making process.

Simulations are available to analyze hypothetical scenarios to improve efficiency, identify areas to improve upon, and to suggest alternative procedures that may help in future decision-making situations, among other things. The simulations are typically, however, either after-the-fact analyses or hypothetical analyses and the output results are unmanageable data spreadsheets that require organization into some format that is useable by a clinician. Existing simulations are not real-time simulations based on real-time actual data relevant to a current situation. Thus, clinicians are not able to easily make a decision based on objective output data that is in a readily useable format.

BRIEF SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Embodiments of the present invention relate to generating simulations using real-time clinical data. The real-time clinical data allows for a simulation to be created based on a current environment experienced by a user. The user may indicate one or more scenarios to apply to the real-time clinical data. A simulation graph is generated that may include an indication of a baseline status and a scenario status. The baseline status indicates an expected result should no changes be made to a current environment. The scenario status indicates an expected result based on the one or more scenarios selected by the user. Multiple simulation graphs for varying areas of interest may be generated and compared to one another such that a user is able to quickly identify efficient solutions.

Accordingly, in one aspect, the present invention is directed to one or more computer storage media storing computer-useable instructions that, when executed by one or more computing devices, cause the one or more computing devices to perform a method. The method includes receiving a user selection of at least one scenario to include in a first simulation graph. Clinical information relevant to the simulation graph is received. The first simulation graph is generated using the clinical information and the graph includes a scenario status. The first simulation graph is then displayed to a user.

In another aspect, the present invention is directed to a graphical user interface (GUI) for displaying simulation graphs. The GUI includes a simulation graph display area including at least one simulation graph generated from real-time clinical data. The simulation graph includes an indication of a scenario status. The GUI also includes a detail display area for displaying one or more scenarios for the at least one simulation graph and one or more area of interest indicators for the at least one simulation graph. The GUI also includes a comparison indicator that, upon selection thereof, navigates a user to a comparison interface including two or more selected simulation graphs.

In yet another aspect, the present invention is directed to one or more computer storage media storing computer-useable instructions that, when executed by one or more computing devices, cause the one or more computing devices to perform a method. The method includes receiving a selection of a first scenario and a first area of interest to include in a first simulation graph. Clinical information relevant to the first simulation graph is received. A selection of a second scenario to associate with a second simulation graph is received along with a selection of a second area of interest to associate with the second simulation graph. A selection of a comparison indicator is received. Both the first and the second simulation graph are generated and are simultaneously displayed.

BRIEF DESCRIPTION OF THE DRAWINGS

The present invention is described in detail below with reference to the attached drawing figures, wherein:

FIG. 5 is a screenshot illustrating a first exemplary simulation library interface, in accordance with an embodiment of the present invention;

FIG. 6 is a screenshot illustrating a second exemplary simulation library interface, in accordance with an embodiment of the present invention;

DETAILED DESCRIPTION

Figure 1:
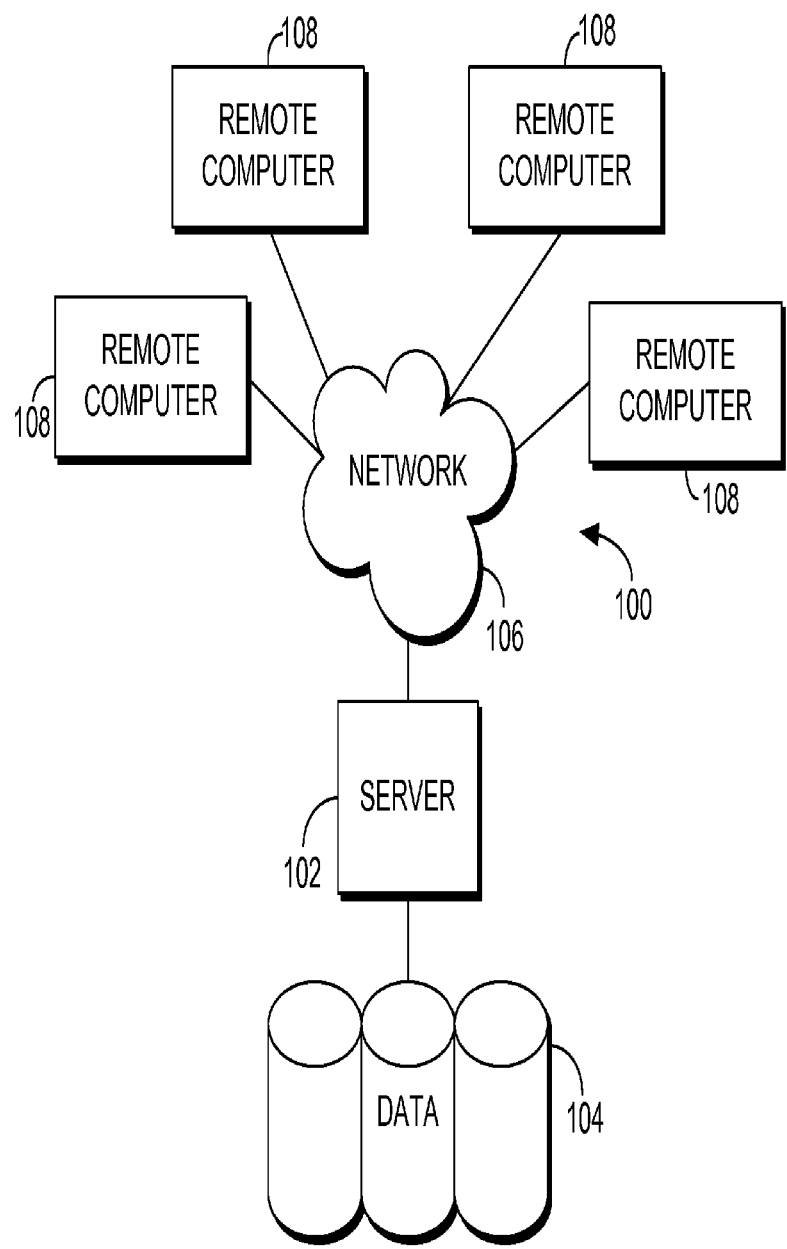
FIG. 1 is a block diagram of an exemplary computing environment suitable for use in implementing the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

Embodiments of the present invention provide for systems, methods, and computer storage media for generating real-time, or near real-time, simulations of healthcare encounters. A real-time simulation, as used herein, refers generally to a simulation including the most up-to-date information. The simulations may utilize real-time data to illustrate the most up-to-date information in a simulation graph, which is a graphical representation of a scenario. Typically, the simulation graph includes at least a scenario status indicating an expected result should one or more scenario variables be applied to the scenario. The simulation graph may also include a baseline status indicating an expected result should no action be taken. For example, if a scenario variable "add a nurse" is selected, the scenario status indicates the results expected if another nurse is added to the scenario. The scenario status may differ from the baseline. This allows users to quickly analyze a current situation and make a decision based on objective output indicating predicted results with one or more scenarios.

Having briefly described embodiments of the present invention, an exemplary operating environment suitable for use in implementing embodiments of the present invention is described below. Referring to the drawings in general, and initially to FIG. 1 in particular, an exemplary computing system environment, for instance, a medical information computing system, on which embodiments of the present invention may be implemented is illustrated and designated generally as reference numeral 100. It will be understood and appreciated by those of ordinary skill in the art that the illustrated medical information computing system environment 100 is merely an example of one suitable computing environment and is not intended to suggest any limitation as to the scope of use or functionality of the invention. Neither should the medical information computing system environment 100 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 100 includes a general purpose computing device in the form of a server 102. Components of the server 102 may include, without limitation, a processing unit, internal system memory, and a suitable system bus for coupling various system components, including database cluster 104, with the server 102. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 102 typically includes, or has access to, a variety of computer-readable media, for instance, database cluster 104. Computer-readable media can be any available media that may be accessed by server 102, and includes volatile and nonvolatile media, as well as removable and non-removable media. By way of example, and not limitation, computer-readable media may include computer storage media and communication media. Computer storage media may include, without limitation, volatile and nonvolatile media, as well as removable and nonremovable media implemented in any method or technology for storage of information, such as computer-readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 102. Communication media typically embodies computer-readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer-readable media.

The computer storage media discussed above and illustrated in FIG. 1, including database cluster 104, provide storage of computer-readable instructions, data structures, program modules, and other data for the server 102.

The server 102 may operate in a computer network 106 using logical connections to one or more remote computers 108. Remote computers 108 may be located at a variety of locations in a medical or research environment, for example, but not limited to, clinical laboratories, hospitals and other inpatient settings, veterinary environments, ambulatory settings, medical billing and financial offices, hospital administration settings, home healthcare environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, genetic counselors, researchers, veterinarians, students, and the like. The remote computers 108 may also be physically located in nontraditional medical care environments so that the entire healthcare community may be capable of integration on the network. The remote computers 108 may be personal computers, servers, routers, network PCs, peer devices, other common network nodes, or the like, and may include some or all of the components described above in relation to the server 102. The devices can be personal digital assistants or other like devices.

Exemplary computer networks 106 may include, without limitation, local area networks (LANs) and/or wide area networks (WANs). Such networking environments are commonplace in offices, enterprise-wide computer networks, intranets, and the Internet. When utilized in a WAN networking environment, the server 102 may include a modem or other means for establishing communications over the WAN, such as the Internet. In a networked environment, program modules or portions thereof may be stored in the server 102, in the database cluster 104, or on any of the remote computers 108. For example, and not by way of limitation, various application programs may reside on the memory associated with any one or more of the remote computers 108. It will be appreciated by those of ordinary skill in the art that the network connections shown are exemplary and other means of establishing a communications link between the computers (e.g., server 102 and remote computers 108) may be utilized.

In operation, a user may enter commands and information into the server 102 or convey the commands and information to the server 102 via one or more of the remote computers 108 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the server 102. In addition to a monitor, the server 102 and/or remote computers 108 may include other peripheral output devices, such as speakers and a printer.

Although many other internal components of the server 102 and the remote computers 108 are not shown, those of ordinary skill in the art will appreciate that such components and their interconnection are well known. Accordingly, additional details concerning the internal construction of the server 102 and the remote computers 108 are not further disclosed herein.

Figure 2:
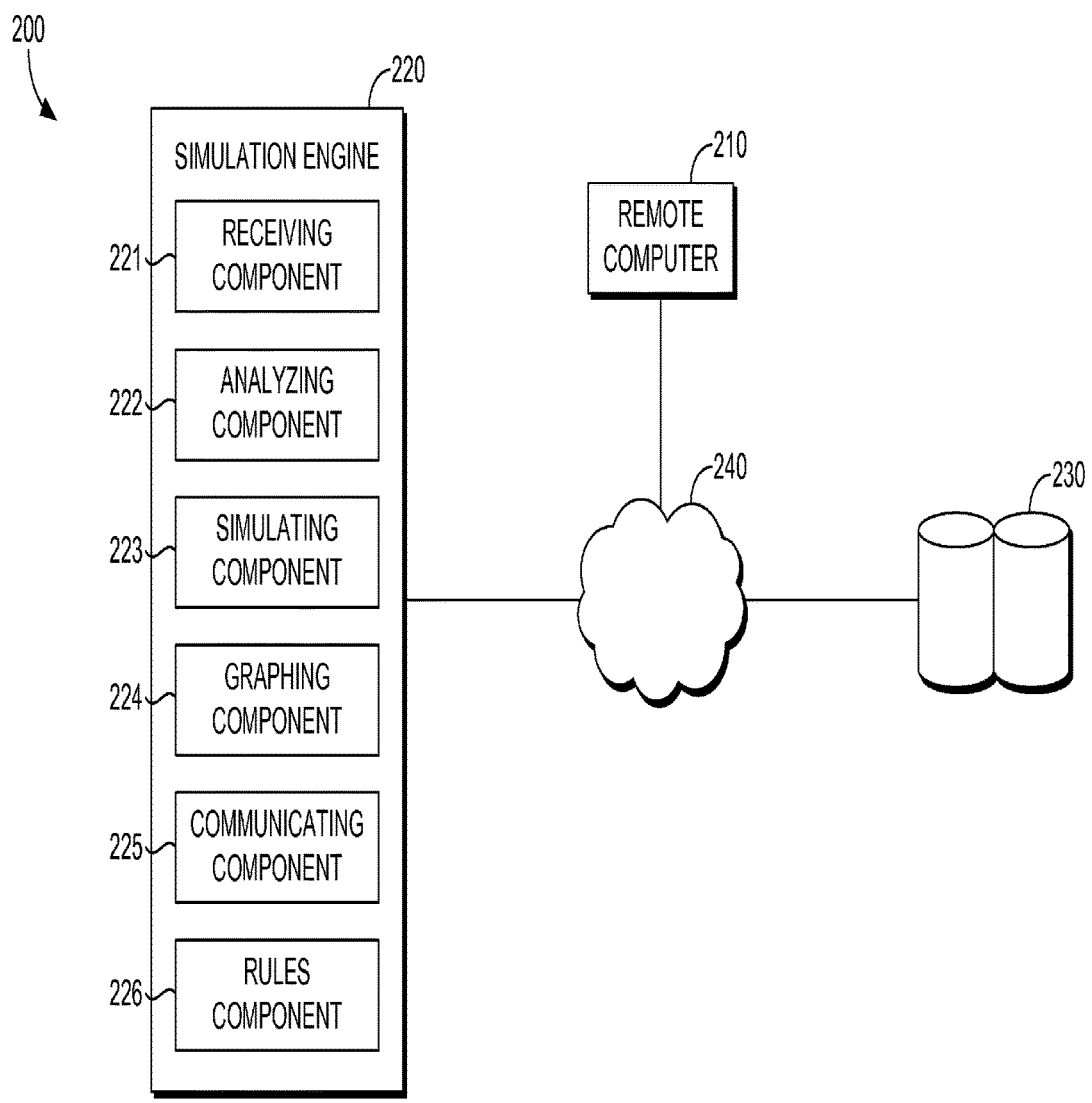
FIG. 2 is an exemplary system architecture suitable to implement embodiments of the present invention.

Turning to FIG. 2, an architectural framework 200 is shown for generating simulations. This architectural framework 200 may operate, for instance, within the context of the exemplary medical information system 100 of FIG. 1. The system of FIG. 2 includes a remote computer 210, a simulation engine 220, a database 230, and a network 240. Other components not shown here may also be used to carry out aspects of the present invention. Further, several components shown in FIG. 2 may be combined into a single component although shown separately in FIG. 2. Alternatively, components, such as the database 230, although shown as a single component, may actually be two or more components.

The simulation engine 220 includes a receiving component 221, an analyzing component 222, a simulating component 223, a graphing component 224, a communicating component 225, and a rules component 226. Each component of the simulation engine 220 may assist in receiving, analyzing, storing, communicating, or the like, information relevant to generate a simulation. The simulation engine 220 may be associated with a healthcare entity. Healthcare entities may include, but are not limited to, clinicians, hospitals, clinics, pharmacies, laboratories, and the like. Throughout this application, the term "user" is used interchangeably with healthcare entities and is not meant to limit the scope of the present invention in any way.

Healthcare simulations are often used to aid users in analyzing efficiency, productivity, and the like. A simulation, as used herein, refers generally to an analysis of an area of interest based on one or more scenario variables using the most up-to-date information relevant to the area of interest. An area of interest, as used herein, refers generally to a category of a healthcare encounter to include in a simulation. For instance, an area of interest may be durations, patients, utilization, wait times, or the like. A scenario variable, as used herein, refers generally to an adjustable variable that impacts the area of interest. For instance, scenario variables include, but are not limited to, changes to staffing, clinician wait times, ancillary turnaround times, bed status/availability, or the like.

In embodiments, the simulation results are depicted in a simulation graph, which is a graphical representation of the simulation results. The simulation graph may include, but is not limited to, a baseline status indicating an expected result for a scenario should no action be taken. For instance, if an area of interest (e.g., length of stay overall) is selected, a baseline status will indicate the predicted length of stay overall should the current environment remain unchanged (i.e., no scenario variables are applied to the scenario). A baseline status is not required in the simulation graph.

The simulation graph may also include at least one scenario status indicating an expected result should one or more scenario variables be applied to the scenario. For example, if a scenario variable "add a nurse" is selected, the scenario status indicates the results expected if another nurse is added to the scenario. In embodiments, the scenario status and the baseline status are simultaneously illustrated in the same simulation graph. By illustrating the baseline status and the scenario status in the same simulation graph, a user is able to quickly identify the effects of the scenario variable.

Returning to FIG. 2, during generation of a healthcare simulation, data is received by the receiving component 221. The receiving component 221 is configured to receive simulation requests from a user. The simulation request may be to view a simulation library, build a new simulation graph, build an analysis group, manage an analysis group, or the like. An analysis group, as used herein, refers generally to a group of simulation graphs that have been associated with one another and include the same scenario variable(s) applied to a scenario. For instance, an analysis group may include a simulation for Length of Stay by Arrival Hour, a simulation for Length of Stay Overall, and a simulation for Average Length of Stay per Day that have each been associated with one another. Each of the simulations may include the same scenario variable(s) as well. For instance, a scenario variable of "Beds +1" (i.e., add a bed) may be included in each of the simulations such that it is easily identified where "Beds +1" has a bigger impact. In embodiments, each graph of an analysis group is simultaneously displayed on a single graphical user interface, as will be described in further detail below.

Once a user has entered a simulation request, the receiving component 221 is further configured to receive simulation specifications from a user input. Simulation specifications, as used herein, refer generally to parameters defining the simulation graph, including the area of interest, the scenario variables, and the like. The simulation specifications are selected and the selections are received by the receiving component 221. In embodiments, the receiving component 221 receives a selection of an area of interest and up to three scenario(s) for the simulation. In further embodiments, a GUI is provided that allows a user to filter scenarios such that the options are narrowed down.

The receiving component 221 is further configured to receive data relevant to the healthcare simulation from the database 230. In embodiments, the database 230 is a clinical database including one or more patient's electronic health records (EHR's) such that the healthcare simulation is based on an actual environment currently experienced by an associated user. The database 230 may further include, but is not limited to, patient documents, patient data, clinical data, clinician information, facility data, operational data, staffing data, analyses, or other types of electronic medical documentation relevant to a particular patient's condition and/or treatment. Data in database 230 may be various types of information relevant to the condition and/or treatment of a particular patient and can include information relating to, for example, patient identification information, images, physical examinations, vital signs, past medical histories, surgical histories, family histories, histories of present illnesses, current and past medications, allergies, symptoms, past orders, completed orders, pending orders, tasks, lab results, other test results, patient encounters and/or visits, immunizations, physician comments, nurse comments, other caretaker comments, and a host of other relevant clinical information. The receiving component 221 may receive the data from the database 230 subsequent to the request so that the simulation includes the most up-to-date information from the database 230.

By way of example only, assume an emergency department (ED) nurse inputs a request to initiate a healthcare simulation to analyze triage time in the ED. The ED nurse may select both an area of interest and one or more scenario variables to modify the area of interest in the simulation. The simulation engine 220 receives, at the receiving component 221, the simulation request, the selected area of interest to be modified by the selected scenario variable(s) in the scenario(s), and clinical data from the database 230 such that the simulation is modeled after the current environment experienced by the ED nurse.

Figure 3:
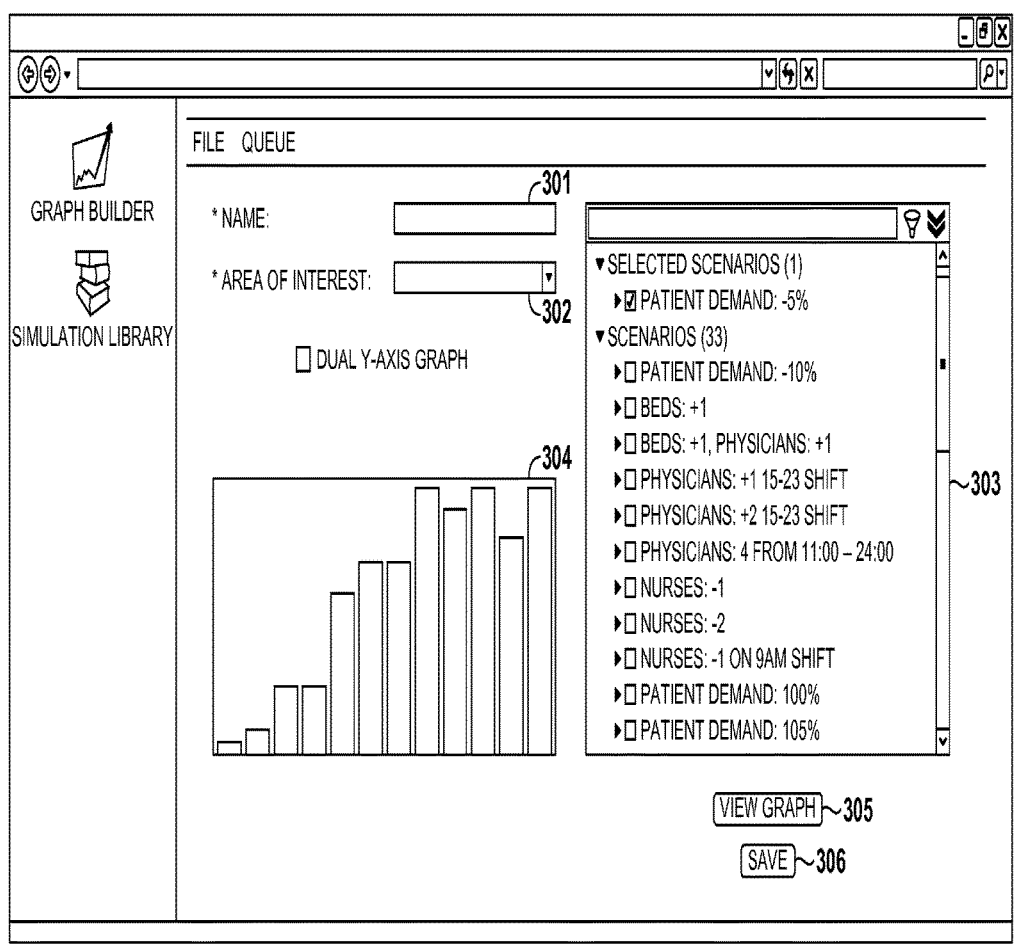
FIG. 3 is a screenshot illustrating an exemplary graph builder interface, in accordance with an embodiment of the present invention.

An exemplary graph builder interface 300 is provided in FIG. 3. The graph builder interface 300 includes a name input area 301, an area of interest input area 302, a scenario display area 303, a preview area 304, a view graph indicator 305, and a save indicator 306. Continuing with the above example, the ED nurse may input a name of the simulation graph into the name input area 301. The ED nurse may also indicate the selected area of interest in the area of interest input area 302. One or more scenarios may be selected from the scenario display area 303. Upon inputting the area of interest and one or more scenarios, the preview area 304 displays a preview of the simulation graph. The ED nurse may then view the scenario by selecting the view graph indicator 305 or save the scenario by selecting the save indicator 306.

Returning to FIG. 2, upon receiving the data, the receiving component 221 communicates the data to the analyzing component 222. The analyzing component 222 is configured to analyze the data received from the database 230 and to identify if the data received should be converted to a different format. Data may need to be converted to a different format to fit a specific methodology or simply to clean up the data such that it is useable by the simulation engine 220. Upon determining that the data should be converted to a different format, the analyzing component 222 communicates the data to a curve-fitting tool (not shown). The curve-fitting tool may be any curve-fitting tool known to one of ordinary skill in the art.

The data is communicated, either directly or through a curve-fitting tool, to the simulating component 223. The simulating component 223 may be any device capable of performing a simulation with input data. The simulation component 223 is configured to receive the real-time data and perform statistical analysis on the data in order to output simulation results. In embodiments, the simulation component 223 is Arena® Simulation Software by Rockwell Automation, Inc.

Once the simulating component 223 has performed a statistical analysis on the real-time data, the results are organized into a simulation graph by the graphing component 224 and communicated to the user by the communicating component 225. The communicating component 225 may communicate the final output to the remote computer 210 to be displayed to a user.

In embodiments, the communicating component 225 is also configured to communicate a proposed action to a user based on predefined scenarios. The predefined scenarios may be scenarios that have been previously executed, reviewed, and/or identified as an appropriate action. A rules component 226 is configured to identify when real-time data is out of range of specified boundaries based, in part, on the predefined scenarios. When the rules component 226 determines that the real-time data is out of range of specified boundaries, the rules component 226 may propose a recommended action based on the predefined scenarios.

For example, assume that a simulation is being performed on ED data. A user could set up the simulation engine 220 to monitor a number of people waiting to be triaged. A user could also indicate a maximum number of people waiting to be triaged that the ED can handle. As the number of people waiting to be triaged approaches the maximum number indicated by the user, the rules component 226 may automatically notify appropriate individuals that the boundary is approaching. The rules component 226 may propose that additional staff be added to the ED or that additional beds be opened in the ED. As the number of people waiting begins to decrease, the rules component 226 may additionally notify the appropriate individuals that they may begin moving back to a normal workflow. The proposed action may be communicated to the user via the communicating component 225.

Figure 4:
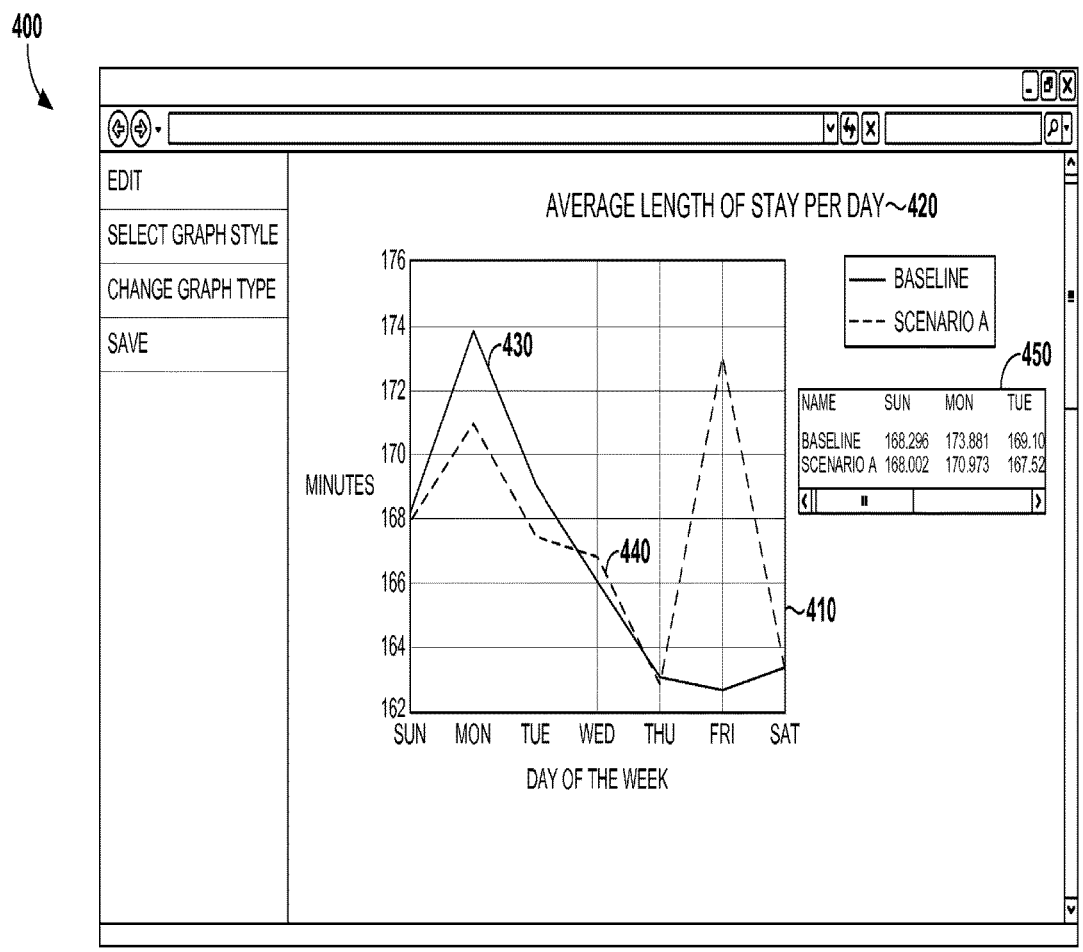
FIG. 4 is a screenshot illustrating an exemplary GUI, in accordance with embodiments of the present invention.

The simulation graph displayed to the user may include a baseline status, at least one scenario status, or the like. An exemplary GUI 400 is illustrated in FIG. 4. The GUI 400 includes a simulation graph 410 that has been generated for an area of interest 420 selected by a user. A baseline status 430 is illustrated in the simulation graph 410 as well as a scenario status 440. The scenario status may be for any scenario variable selected by the user such as, for example, adding a bed or a nurse. The GUI 400 may also include a raw data display area 450 that indicates the actual data utilized to create the simulation graph 410. As also indicated in GUI 400, the user is able to save the simulation graph 410, change the graph type (e.g., bar graphs, line graphs, etc.), and edit styles of the graph (e.g., fonts, colors, etc.). In embodiments, a baseline status is not included in a simulation graph.

When a user chooses to save a simulation graph, the graph may be saved in a simulation library. The simulation library may include saved simulation graphs and saved analysis groups. An exemplary simulation library interface 500 is provided in FIG. 5. A user may search for items from within the simulation library. In embodiments, a filter tool is available to assist a user with searching.

As previously indicated, the simulation library interface 500 may include saved simulation graphs and analysis groups. The simulation library interface 500 may also include a new indicator 510, an add to group indicator 520, and a comparison indicator 530. New items may be added to the simulation library from within the simulation library upon selection of the new indicator 510. For example, assume a user selected the new indicator 510 to create a new analysis group. Upon selection of the new indicator 510, a name prompt 610, as indicated in a simulation library interface 600 of FIG. 6, is displayed. The user may then input a name of the new analysis group into the name prompt 610.

Figure 7:
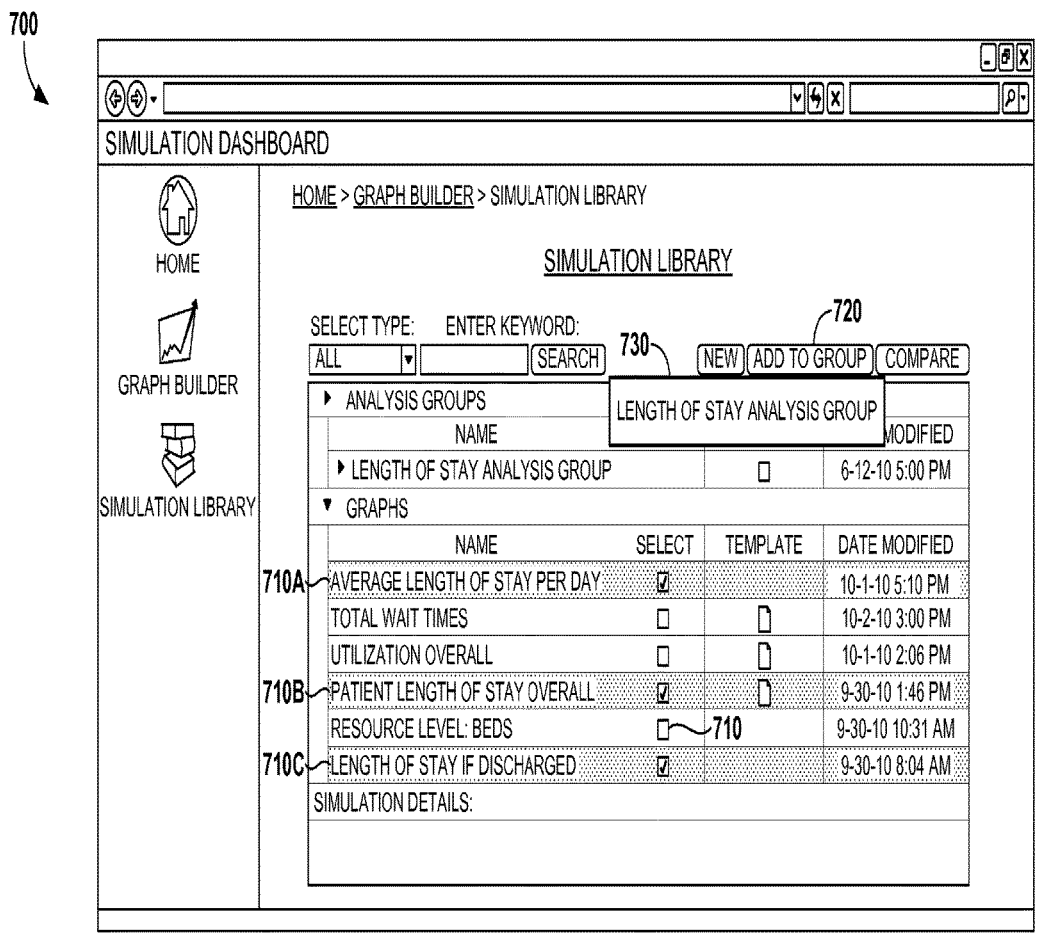
FIG. 7 is a screenshot illustrating an exemplary analysis group interface, in accordance with an embodiment of the present invention.

A user may wish to add specific simulation graphs to an analysis group. An exemplary analysis group interface 700 is provided in FIG. 7. The analysis group interface 700 includes one or more graph selection input areas 710. A user may select the graph selection input area 710 associated with a specific graph that is desired to be added to an analysis group. As illustrated in FIG. 7, graphs 710A, 710B, and 710C have each been selected to add to an analysis group since their corresponding graph selection input areas have been selected. A user may then select the add to group indicator 720 in order to add the selected graphs to an analysis group. An analysis group selection window 730 is displayed upon selection of the add to group indicator 720 in order for a user to select an analysis group to which the selected graphs are to be added.

Figure 8:
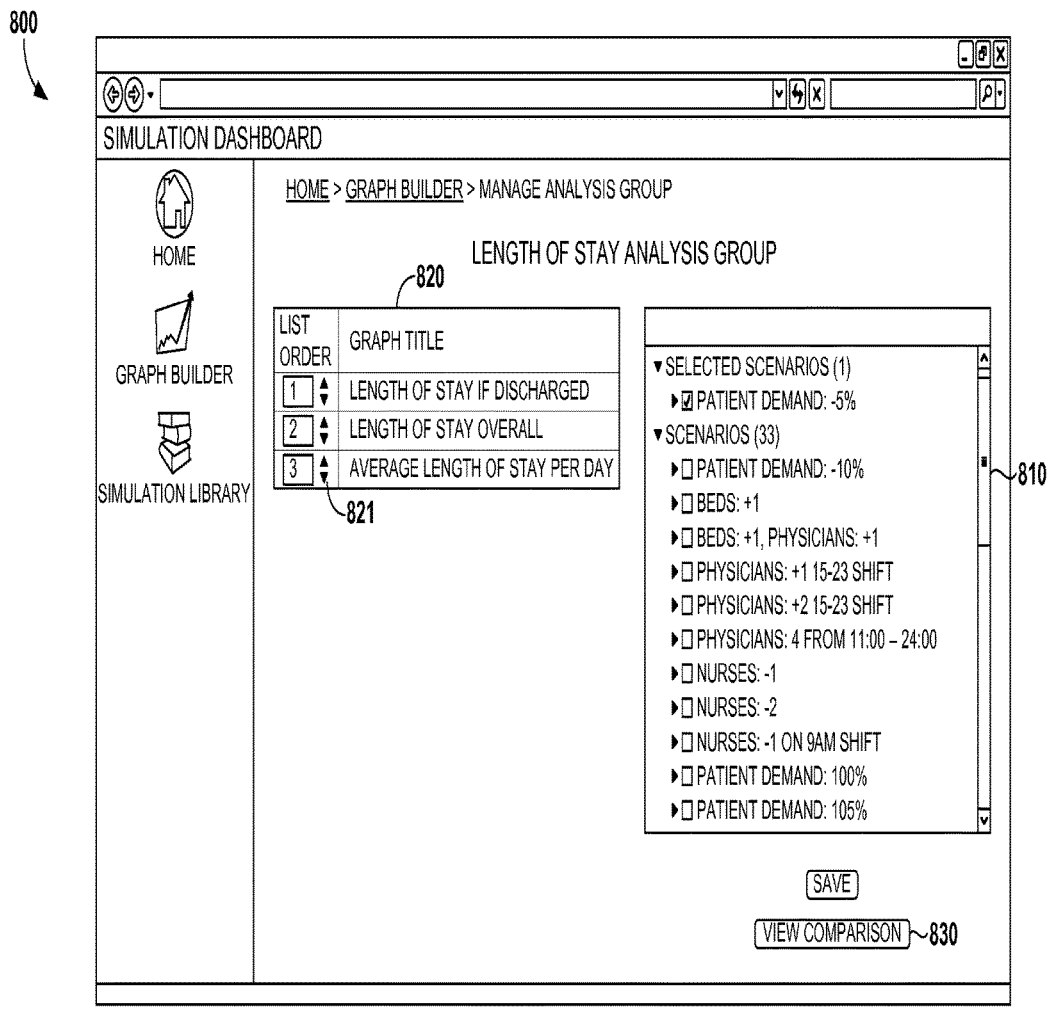
FIG. 8 is a screenshot illustrating an exemplary analysis group management interface, in accordance with an embodiment of the present invention.

Turning to FIG. 8, the analysis groups may be edited from within an analysis group management interface 800. The analysis group management interface 800 may include, but is not limited to, a scenario display area 810 and an analysis group display area 820. The scenario display area 810 provides one or more scenarios that may be applied to the graphs within the analysis group. As described above, an analysis group includes graphs for varying areas of interest that all include the same scenarios. Thus, scenarios selected from the scenario display area 810 are applied to each of the graphs included in the analysis group.

Figure 9:
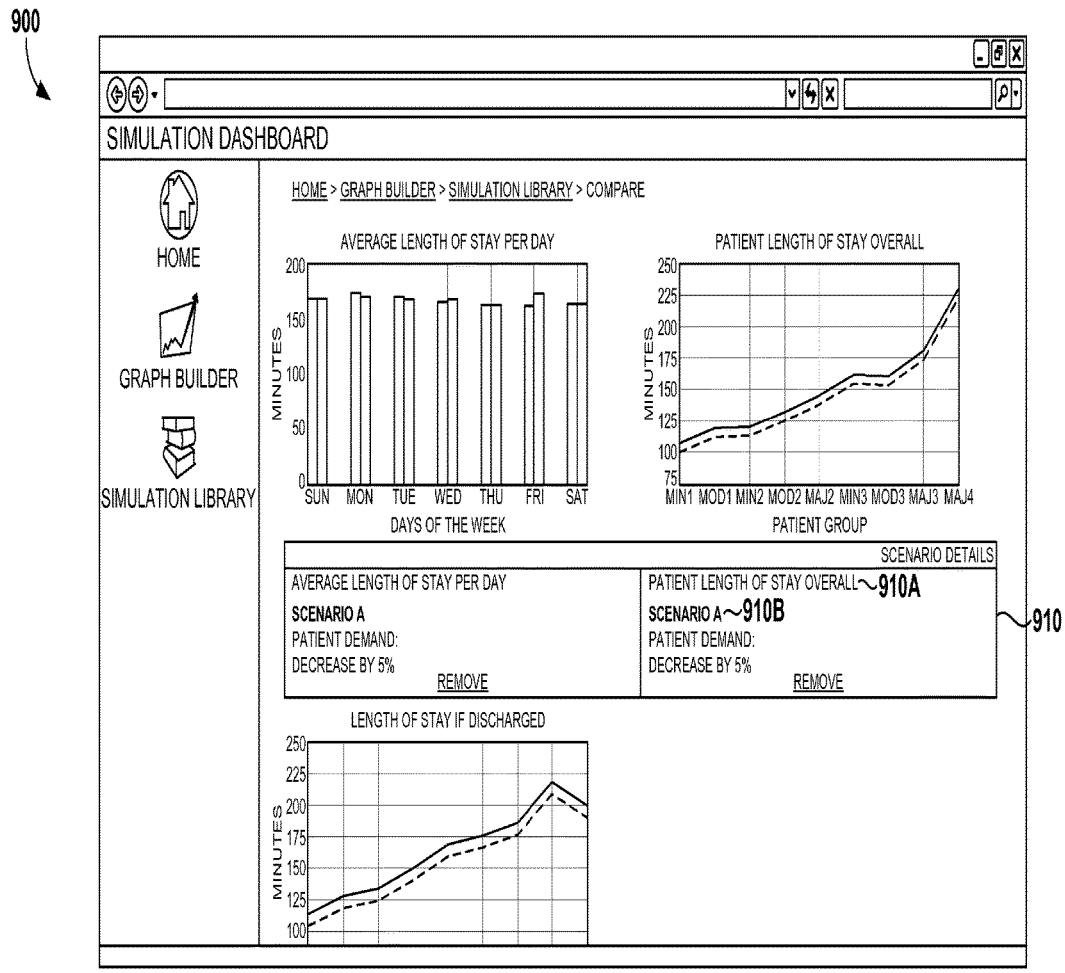
FIG. 9 is a screenshot illustrating an exemplary analysis group comparison interface, in accordance with an embodiment of the present invention.

The analysis group display area 820 includes each graph included in the analysis group and may further include order indicators 821 to adjust the order of the graphs and a view comparison indicator 830 to view a comparison of the graphs of the analysis group. Upon selection of the view comparison indicator 830, the graphs of the analysis group are displayed to the user in an analysis group comparison interface 900, as shown in FIG. 9. Each graph of the analysis group is displayed including a scenario status for each selected scenario(s). The analysis group comparison interface 900 may include a detail display area 910 that provides details for each graph displayed. For instance, the detail display area 910 may include an area of interest display area 910A and an applied scenario display area 910B. In embodiments, a user may be directed to the analysis group comparison interface 900 upon selecting an analysis group from the simulation library interface 500 of FIG. 5 and selecting the comparison indicator 530 of FIG. 5.

Figure 10:
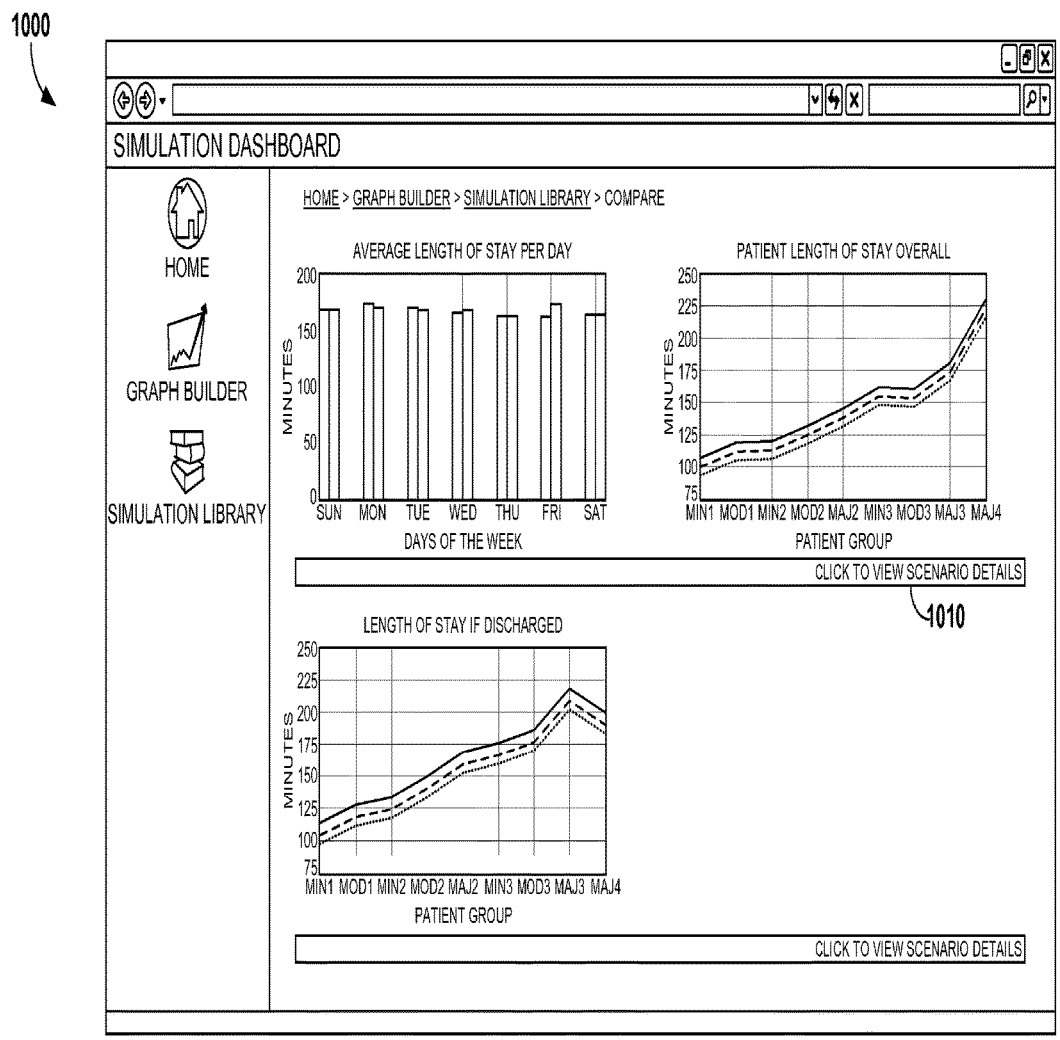
FIG. 10 is a screenshot illustrating an exemplary comparison interface, in accordance with an embodiment of the present invention.

A user may also desire to select individual graphs for display that may not be included in an analysis group. For instance, a user may select individual graphs, whether they are part of an analysis group or not, for display. For example, one or more graphs may be selected from within the simulation library interface 500 of FIG. 5. A user may then select the comparison indicator 530. Upon selection of the comparison indicator 530, a comparison interface 1000 is displayed, as provided in FIG. 10. The graphs displayed in the comparison interface 1000 may include the same scenario variables as one another. In embodiments, the scenario variables are different for each graph. The comparison interface 1000 may include a detail display indicator 1010. Selection of the detail display indicator 1010 may provide details of the individual graphs, similar to the detail display area 910 provided in FIG. 9.

In additional embodiments, a user is able to designate a time interval with which to monitor one or more simulation graphs. For instance, a user may create a simulation graph (or a plurality of simulation graphs for comparison) and desire to monitor the simulation graph(s) over time. Assume, for example, that that a user in an ED would like to monitor the effect of adding an extra nurse to the ED throughout a particular shift. By designating a time interval with which to monitor the simulation graph(s), the simulation graph(s) can be updated according to the designated time interval. Thus, real-time clinical information is accessed according to the designated time interval, as well, ensuring that the updated simulation graph(s) illustrates the most up-to-date environment.

Additionally, a user may be notified when the simulation graph(s) are updated. The notifications may be, for example, pop-up notifications, electronic mail messages, text messages, any message sent to a mobile device, or any other means of notification known by one of skill in the art.

Figure 11:
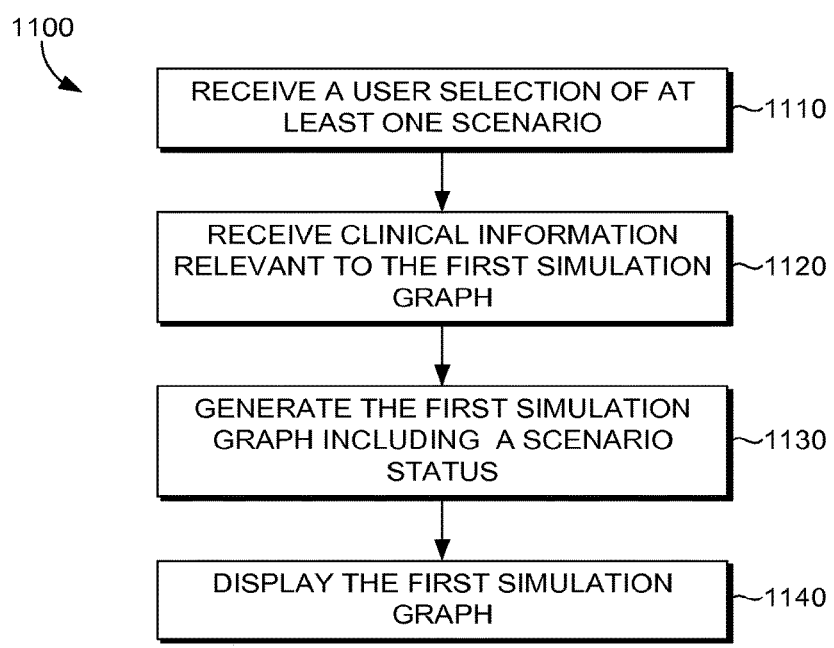
FIG. 11 is a flow diagram illustrating a first exemplary method for generating a real-time simulation.

Referring to FIG. 11, a flow diagram showing a method 1100 for generating real-time simulations, in accordance with an embodiment of the present invention, is provided. Initially, at block 1110, a user selection of at least one scenario is received. At block 1120, clinical information relevant to the first simulation graph is received. At block 1130, the first simulation graph is generated that includes a scenario status. At block 1140, the first simulation graph is displayed.

Figure 12:
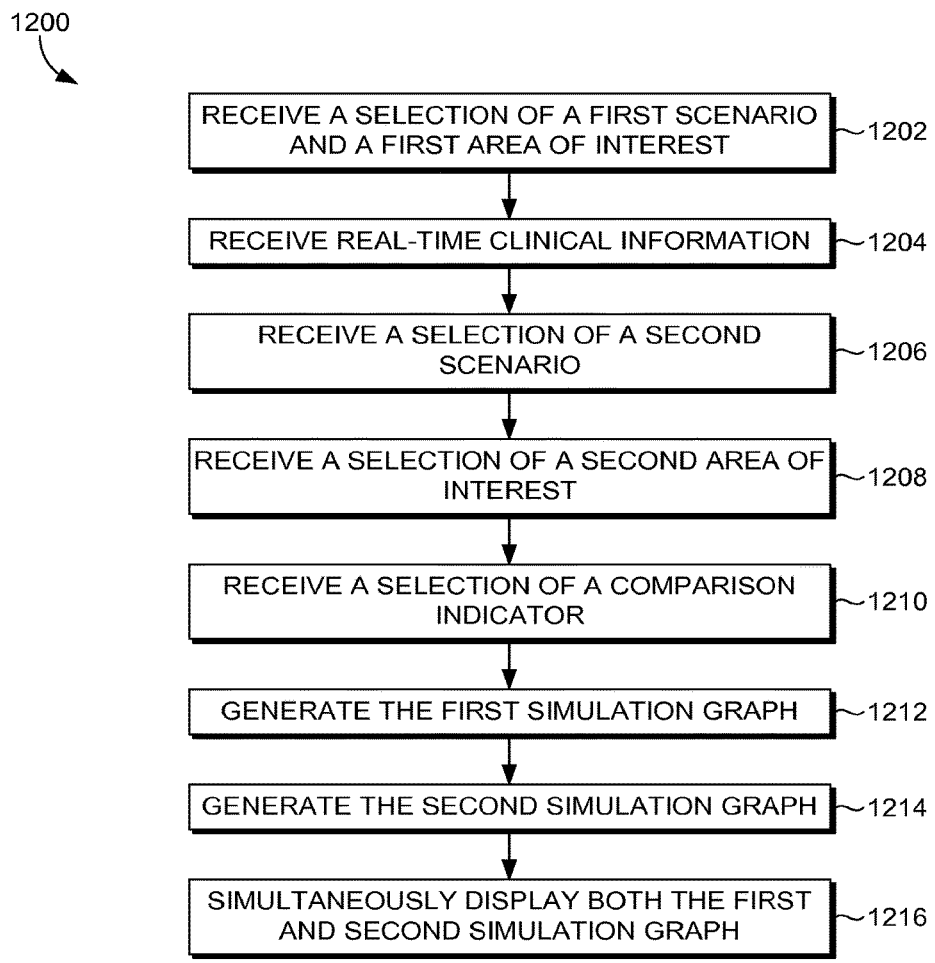
FIG. 12 is a flow diagram illustrating a second exemplary method for generating a real-time simulation.

Referring to FIG. 12, a flow diagram showing a method 1200 for generating real-time simulations, in accordance with an embodiment of the present invention, is provided. Initially, at block 1202, a selection of a first scenario and a first area of interest are received. At block 1204, clinical information relevant to the first simulation graph is received. A selection of a second scenario is received at block 1206 and a selection of a second area of interest is received at block 1208. A selection of a comparison indicator is received at block 1210. The first and second simulation graphs are generated at blocks 1212 and 1214. Both the first simulation graph and the second simulation graph are simultaneously displayed at block 1216.

The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and subcombinations are of utility and may be employed without reference to other features and subcombinations. This is contemplated and within the scope of the claims.

What is claimed is:

1. One or more non-transitory computer storage media storing computer-useable instructions that, when executed by one or more computing devices, cause the one or more computing devices to perform a method comprising:
 receiving a user selection of at least one scenario to include in a first simulation graph;
 receiving relevant real-time clinical information relevant to the first simulation graph, wherein the relevant real-time clinical information includes information from one or more patients' electronic medical records;
 generating the first simulation graph that includes a scenario status that is based on the at least one scenario and the relevant real-time clinical information;
 displaying the first simulation graph;
 monitoring, using a rules component, the relevant real-time clinical information;
 identifying, using the rules component, when the relevant real-time clinical information is approaching one or more specified boundaries based at least on a predefined scenario;
 automatically notifying, using the rules component, the one or more users when the relevant real-time clinical information is approaching one or more out of range specified boundaries, wherein the notification includes at least one first recommended action; and
 automatically notifying, using the rules component, the one or more users when the relevant real-time clinical information is returning to a value within the range of the one or more specified boundaries, wherein the notification includes at least one second recommended action.

2. The non-transitory computer storage media of claim 1, wherein the at least one scenario is a modification to staffing, bed availability, clinician time, or ancillary time.

3. The non-transitory computer storage media of claim 1, wherein the at least one scenario is one of adding a bed or adding a clinician.

4. The non-transitory computer storage media of claim 1, wherein the first simulation graph further includes a baseline status that indicates an expected result.

5. The non-transitory computer storage media of claim 1, wherein the scenario status indicates an expected result based on the at least one scenario.

6. The non-transitory computer storage media of claim 1, further comprising saving the first simulation graph.

7. The non-transitory computer storage media of claim 1, further comprising receiving a user selection of a second scenario to include in a second simulation graph;
 generating the second simulation graph based on the relevant clinical information and the second scenario; and
 displaying the second simulation graph.

8. The non-transitory computer storage media of claim 7, wherein the second scenario is the same as the at least one scenario.

9. The non-transitory computer storage media of claim 7, wherein the second scenario is different from the at least one scenario.

10. The non-transitory computer storage media of claim 1, further comprising:
 receiving a user selection of each of the first and second simulation graphs;
 receiving a selection of a comparison indicator;
 in response to receiving the selection of the comparison indicator, simultaneously displaying both the first simulation graph and the second simulation graph.

11. One or more non-transitory computer storage media storing computer-useable instructions that, when executed by one or more computing devices, cause the one or more computing devices to display a graphical user interface (GUI), said GUI comprising:
 a graph builder interface for building a simulation graph, comprising:
  a name input area;
  an area of interest input area;
  a scenario display area;
  a preview area;
  a view graph indicator; and
  a save indicator;
 an analysis group interface for selecting one or more analysis groups comprising:
  a simulation graph selection area that allows for selection of one or more simulation graphs to be included in the one or more analysis groups; and
  a time interval selection area for selection of a time interval for updating the one or more simulation graphs with relevant real-time clinical information;
 a simulation library interface for interacting with one or more saved simulation graphs and one or more saved analysis groups, comprising:
  a new graph indicator;
  an add to group indicator;
  a comparison indicator for selecting for display two or more simulation graphs; and
 a simulation graph display area for presenting at least one simulation graph of the one or more simulation graphs, the one or more simulation graphs including the relevant real-time clinical data, wherein each simulation graph includes each of an indication of a scenario status and a baseline status indicating an expected result;
 a rules component that monitors the relevant clinical information; and
 a notification area that presents automatic notifications, based on the rules component, the automatic notifications comprising:
  an out of range notification that indicates when the relevant real-time clinical information is approaching one or more out of range specified boundaries, wherein the out of range notification includes at least one first recommended action; and
  a return to range notification that indicates when the relevant real-time clinical information is returning to a value within the range of the one or more specified boundaries, wherein the return to range notification includes at least one second recommended action.

12. The GUI of claim 11, wherein each of the two or more selected simulation graphs is associated with the same scenario.

13. The GUI of claim 11, wherein each of the two or more selected simulation graphs is associated with one or more scenarios that differ from one another.

14. The GUI of claim 11, further comprising a notification area that presents automatic notifications, the automatic notifications comprising:
   an out of range notification that indicates when the relevant real-time clinical information is approaching one or more out of range specified boundaries; and
   a return to range notification that indicates when the relevant real-time clinical information is returning to a value within the range of the one or more specified boundaries.

15. The GUI of claim 11, further comprising a detail display area for displaying:
   one or more scenarios for the at least one simulation graph; and
   one or more area of interest indicators for the at least one simulation graph.

16. A computer system for notifying clinicians when real-time clinical information is approaching a boundary for at least one predefined scenario, the system comprising:
   at least one computing device having a processor coupled to a memory, the at least one computing device including the following:
   a receiving component for:
      receiving a selection of a first scenario and a first area of interest to include in a first simulation graph;
      receiving a selection of a second scenario to associate with a second simulation graph, wherein the second scenario is the same as the first scenario;
      receiving a selection of a second area of interest to associate with the second simulation graph, wherein the second area of interest is different than the first area of interest;
      receiving a selection of a comparison indicator; and
      receiving relevant real-time clinical information, the relevant real-time clinical information being relevant to the first simulation graph and the second simulation graph, wherein the relevant real-time clinical information includes information from one or more patients' electronic medical records;
   a simulating component configured to perform a statistical analysis on he selections and information received by the receiving component and to output simulation results;
   a graphing component for:
      generating the first simulation graph, including a first scenario status, based on at least the first scenario and the relevant real-time clinical information; and
      generating the second simulation graph, including a second scenario status, based on at least the second scenario and the relevant real-time clinical information;
   a communicating component for simultaneously displaying both the first simulation graph and the second simulation graph; and
   a rules component for:
      monitoring the relevant real-time clinical information;
      identifying when the relevant real-time clinical information is approaching one or more out of range specified boundaries based at least on a predefined scenario associated with at least one of the first simulation graph and the second simulation graph;
      automatically notifying one or more users when the relevant real-time clinical information is approaching the one or more out of range specified boundaries, wherein the notification includes at least one first recommended action; and
      automatically notifying the one or more users when the relevant real-time clinical information is returning to a value within the range of the one or more out of range specified boundaries, wherein the notification includes at least one second recommended action.

17. The computer system of claim 16, further comprising an analyzing component configured to identify when the selections and information received by the receiving component need to be converted to a different format and to convert the selections and information to the different format.

18. The computer system of claim 16, wherein the rules component is configured to generate and present an expected result based on both the first scenario status and the second scenario status.

19. The computer system of claim 16, wherein the first scenario is a modification to staffing, bed availability, clinician time, or ancillary time.

20. The computer system of claim 16, wherein the second scenario is a modification to staffing, bed availability, clinician time, or ancillary time.

* * * * *

UNITED STATES PATENT AND TRADEMARK OFFICE
CERTIFICATE OF CORRECTION

PATENT NO. : 10,268,784 B2
APPLICATION NO. : 14/804963
DATED : April 23, 2019
INVENTOR(S) : Amber Buchan et al.

Page 1 of 1

It is certified that error appears in the above-identified patent and that said Letters Patent is hereby corrected as shown below:

In the Specification

Column 10, Line 32: delete "that that" and replace with --that--.

In the Claims

Column 13, Line 44 Claim 16: delete "he" and replace with --the--.

Signed and Sealed this
Eighteenth Day of June, 2019

Andrei Iancu
*Director of the United States Patent and Trademark Office*